United States Patent

Tanaka et al.

[11] Patent Number: 5,888,828
[45] Date of Patent: Mar. 30, 1999

[54] KIT FOR MEASURING UREA NITROGEN

[75] Inventors: Hirotoshi Tanaka; Ryo Kojima; Katsuhiro Katayama, all of Fukushima-ken, Japan

[73] Assignee: Nitto Boseki Co., Ltd., Japan

[21] Appl. No.: 928,255

[22] Filed: Sep. 12, 1997

[30] Foreign Application Priority Data

Oct. 2, 1996 [JP] Japan .................................. 8-261505

[51] Int. Cl.$^6$ .................................................. G01N 33/62
[52] U.S. Cl. .......................... 436/108; 435/12; 436/106; 436/120; 436/171; 422/61; 422/82.05
[58] Field of Search .............. 435/12; 436/106, 436/108, 120, 171; 422/61, 82.05

[56] References Cited

U.S. PATENT DOCUMENTS

| Re. 29,725 | 8/1978 | Johnson et al. ........................ 23/230 R |
| 4,189,536 | 2/1980 | Green .......................................... 435/12 |
| 4,229,369 | 10/1980 | Green ................................. 260/501.19 |
| 4,394,449 | 7/1983 | Modrovich .............................. 435/188 |
| 4,753,882 | 6/1988 | Takeshio et al. ........................ 435/228 |
| 5,008,078 | 4/1991 | Yaginuma et al. ........................ 422/56 |

FOREIGN PATENT DOCUMENTS

B-3-65160 8/1984 Japan .
A-2-255099 10/1990 Japan .
A-59-1591900 10/1991 Japan .

OTHER PUBLICATIONS

English Translation of Japanese Patent JP 59–151900.
English Translation of Japanese Patent JP 02255099.
English Translation of Japanese Patent JP 03065160.

Primary Examiner—Lyle A. Alexander
Assistant Examiner—S. Carrillo
Attorney, Agent, or Firm—Nixon & Vanderhye

[57] ABSTRACT

A method of measuring urea nitrogen on the basis of the ultraviolet absorption of urease-GLDH by a reaction rate method, which method not only permits accurate measurement of a sample containing a high concentration of urea nitrogen but also permits accurate measurement of a sample containing polyols such as mannitol without suffering the influence of the polyols, the method comprising hydrolyzing urea in a sample with urease, reacting glutamate dehydrogenase (GLDH) with ammonia formed by the hydrolysis, in the presence of α-ketoglutaric acid (α-KG) and reduced-type nicotineamide adenine dinucleotide (NADH) or reduced-type nicotineamide adenine dinucleotide phosphate (NADPH), and measuring the reduced-type nicotineamide adenine dinucleotide (NADH) or reduced-type nicotineamide adenine dinucleotide phosphate (NADPH) for a decrease rate to measure urea nitrogen derived from the urea, and characterized in that a sulfhydryl compound is co-present with the urease.

2 Claims, 2 Drawing Sheets

KIT FOR MEASURING UREA NITROGEN

FIELD OF THE INVENTION

The present invention relates to a method of measuring urea nitrogen in a sample and a reagent therefor. More specifically, it relates to a method of measuring urea nitrogen, which method is applicable for the measurement of a sample containing a high concentration of urea nitrogen and further, which is free from an influence by polyols contained in the sample, and a reagent for the above measurement.

PRIOR ART

It is known that the amount of utea nitrogen in a biosample, etc., varies depending upon renal functional disorders such as renal failure or hepatic functional disorders such as hepatocirrhosis, and the measurement thereof is an index important for medical diagnosis and making the state of an illness clear and further for determining the course of various therapeutical treatments. In recent years, due to accuracy and specificity, there is widely employed a method of measuring urea nitrogen ("urease-GLDH method" hereinafter) in which urea is hydrolyzed by a urease reaction, α-ketoglutaric acid ("α-KG" hereinafter), either reduced-type nicotineamide adenine dinucleotide ("NADH" hereinafter) or reduced-type nicotineamide adenine dinucleotide phosphate ("NADPH" hereinafter) and glutamate dehydrogenase ("GLDH" hereinafter) are reacted with formed ammonia, and the amount of decreased NADH or NADPH is measured as a change in the absorption of an ultraviolet portion.

Further, an automatic analyzer has been being remarkably developing in recent years, and it is therefore desired to develop a method of measuring urea nitrogen by a reaction rate method in which a measurement result can be obtained in a short period of time and the measurement is almost free from an influence caused by an interference substance in a sample.

Meanwhile, the reaction rate method is applicable when the Km value of urease to urea is sufficiently greater than an urea concentration in a measuring system, and a high concentration of urea can be measured. When the measurement is carried out by the reaction rate method, generally, the Km value of urease is too small in many cases, and therefore, an inhibitor is added for increasing an apparent Km value in some cases. As an urea nitrogen measurement method using the above inhibitor, there is known a method using boric acid or its salt asan urease inhibitor (JP-B-03-65160). This method is applicable for accurately measuring a high concentration of urea. It is considered that boric acid forms a chelate complex by mutual activities with a sugar chain in an enzyme and consequently exhibits an inhibition activity.

However, the above method using boric acid or its salt as an urease inhibitor has the following problem. When polyols such as mannitol, etc., are present in a sample, boric acid forms a chelate complex with the polyol, and the inhibition activity against urease substantially does not work. In the measurement of urea nitrogen, therefore, an increase in a measurement value is observed, and no accurate measurement is possible. In fact, mannitol preparations are frequently used as a brain hypotensive agent or a diuretic for clinical treatments. Mannitol is not metabolized in an organism and easily filtered in glomerulus, and it is not re-absorbed in uriniferous tubule, so that a nearly total amount thereof is excreted into urine in a concentrated form. In this case, the mannitol concentration is assumed to amount up to 20%, i.e., 200 mg/ml. When a sample containing mannitol is measured for an urea nitrogen, the above phenomenon causes a serious problem.

SUMMARY OF THE INVENTION

In view of the above problems, it is an object of the present invention to provide a method of accurately measuring urea nitrogen in a sample containing polyols such as mannitol, etc., or in a sample containing a high concentration of urea nitrogen.

For overcoming the defects of the known methods, the present inventors have made diligent studies for a novel urease inhibitor which can replace the boric acid. As a result, it has been found that, in the quantitative determination of urea nitrogen by an urease-GLDH method using a reaction rate method, the presence of a sulfhydryl compound as an inhibitor is effective for overcoming the problems, and the present invention has been accordingly completed. In the presence thereof, the Km value of urease is increased, so that a high concentration of urea nitrogen can be measured, and the influence caused by the above polyols such as mannitol, etc., can be avoided.

That is, the first gist of the present invention consists in a method of measuring urea nitrogen, which comprises hydrolyzing urea in a sample with urease, reacting glutamate dehydrogenase (GLDH) with ammonia formed by the hydrolysis, in the presence of α-ketoglutaric acid (α-KG) and reduced-type nicotineamide adenine dinucleotide (NADH) or reduced-type nicotineamide adenine dinucleotide phosphate (NADPH), and measuring the reduced-type nicotineamide adenine dinucleotide (NADH) or reduced-type nicotineamide adenine dinucleotide phosphate (NADPH) for a decrease rate to measure urea nitrogen derived from the urea, the method characterized in that a sulfhydryl compound is co-present with the urease. (to be referred to as "the method of the present invention" hereinafter).

Further, the second gist of the present invention consists in a kit for measuring urea nitrogen, comprising, as constituents, i) α-ketoglutaric acid (α-KG),
ii) reduced-type nicotineamide adenine dinucleotide (NADH) or reduced-type nicotineamide adenine dinucleotide phosphate (NADPH),
iii) glutamate dehydrogenase (GLDH)
iv) a sulfhydryl compound, and
v) urease (to be referred to as "the kit of the present invention" hereinafter).

DETAILED DESCRIPTION OF THE INVENTION

Figure 1:
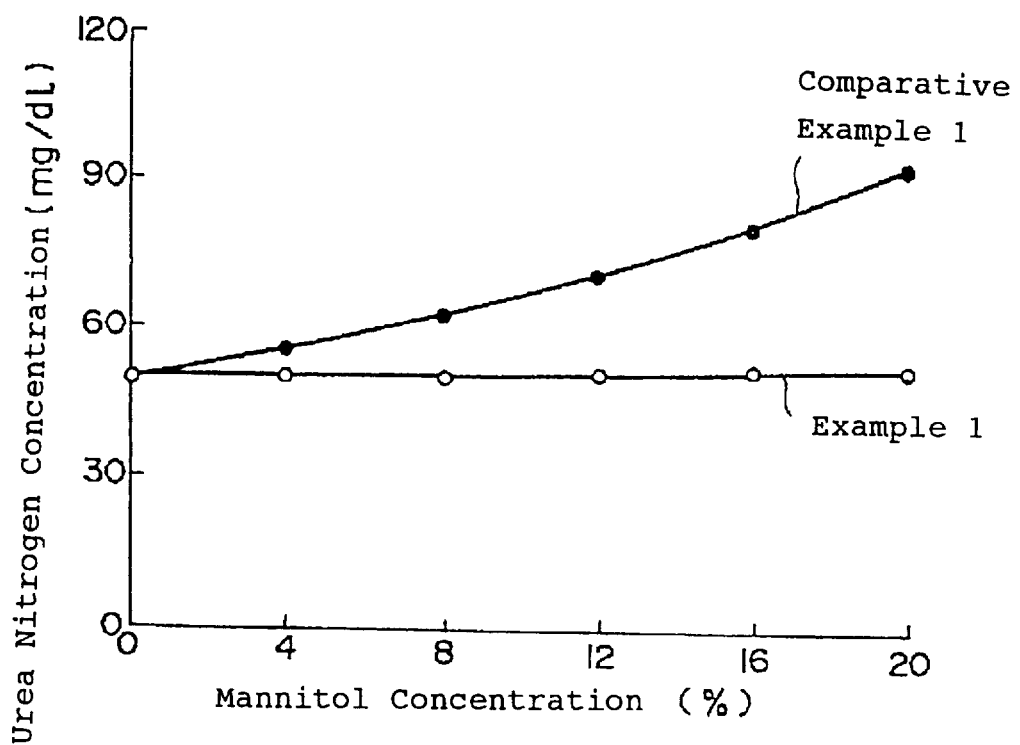
FIG. 1 shows influences caused by mannitol on results of urea nitrogen measurements in Example 1 and Comparative Example 1.
Figure 2:
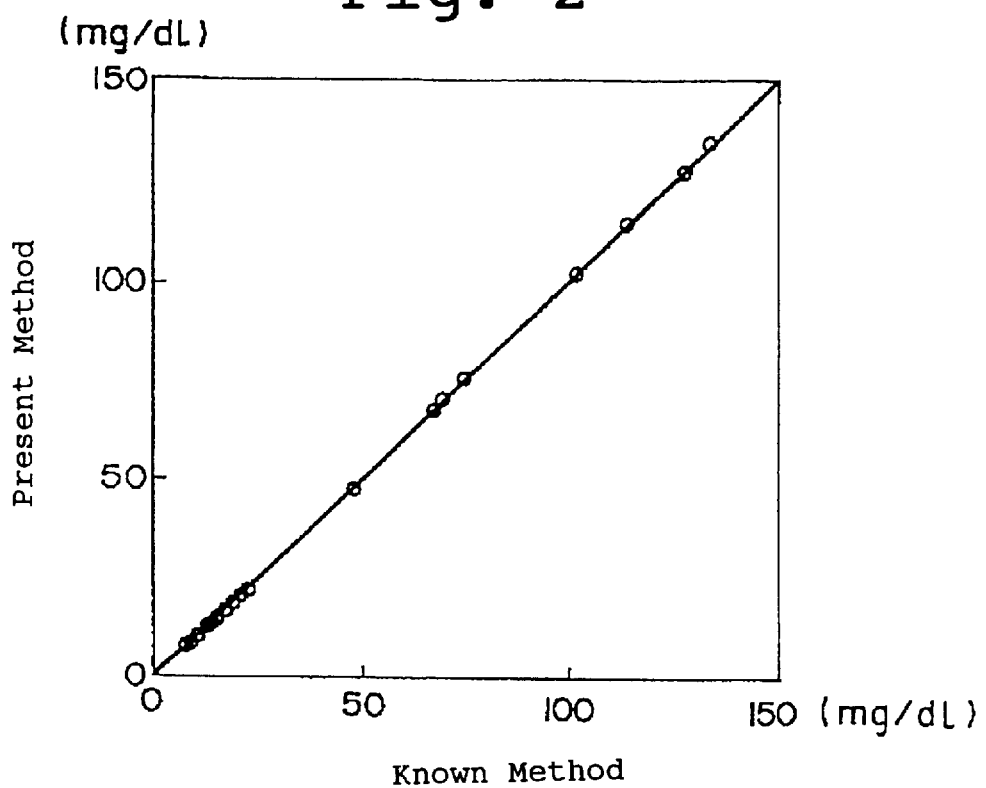
FIG. 2 shows a correlation of results of urea nitrogen measurements by the method of the present invention (axis of ordinates) and by a known method (axis of abscissas).

In the present invention, urea nitrogen can be measured, and a reagent for the measurement of urea nitrogen can be prepared, in the same manner as in conventional techniques except that the reagent contains a sulfhydryl compound together with urease. For example, ammonia present in a sample can be eliminated in a pre-treatment before urease and a sulfhydryl compound are allowed to react.

In the method of the present invention, for increasing the accuracy of measurement, it is preferred to eliminate ammonia in a sample before the measurement of urea nitrogen by reacting GLDH with the ammonia in the presence of α-KG and NADH or NADPH. Since the constitution of a reagent for the elimination of ammonia overlap the constitution of the reagent for the measurement of urea nitrogen, the reagent for the elimination of ammonia can be directly used for the measurement of urea nitrogen.

In the method of the present invention, the sample is not specially limited so long as it contains an urea component. Examples of the sample include plasma, serum, urine, and a solution prepared by diluting each of them.

The sulfhydryl compound that can be used in the method of the present invention includes thioglycerol, thiomalic acid, thioglycolic acid, mercaptoethanol, 3-mercaptopropionic acid, thiophenol, cysteine, N-acetylcysteine, reduced-type glutathione, dithiothreitol and dithioerythritol. Thioglycerol is preferred as a sulfhydryl compound, since thioglycerol generates less odor and is stable.

The concentration of the sulfhydryl compound should be properly adjusted depending upon the kind of a compound, the kind of a sample, measuring conditions and other factors, while it is generally in the range of from 0.1 to 1,000 mM, preferably 1 to 500 mM, particularly preferably 10 to 500 mM.

The concentration of each of α-KG, either NADH or NADPH, GLDH and urease used in the method of the present invention varies depending upon the amount of ammonia which is present in a sample in advance and the amount of urea to be measured, while proper concentrations thereof can be selected as required. For example, the amount of α-KG is generally in the range of from 0.1 to 50 mM, preferably 1 to 30 mM. The amount of NADH or NADPH is generally in the range of from 0.05 to 5 mM, preferably 0.1 to 1 mM, and the amount thereof is set in a range where the limit of absorbance is not exceeded. Although not specially limited, GLDH is preferably derived from a bovine liver or bacteria. The concentration of GLDH is in the range of from 0.1 to 100 units/ml(u/ml), preferably 0.5 to 70 units/ml. The origin of urease is not specially limited, while the urease includes those derived from a jack bean and bacteria. The concentration of urease is 0.1 to 100 units/ml, preferably 0.5 to 50 units/ml, and a proper concentration thereof should be selected depending upon the amount of the sulfhydryl compound.

In the method of the present invention, the pH in the measurement of urea nitrogen is adjusted to a pH of 6 to 10, preferably a pH in the range of 7 to 10. The pH is adjusted with a general buffer solution, and the buffer solution that can be used is selected from a tris buffer solution, a hydrochloric acid buffer solution, a phosphoric acid buffer solution, a carbonic acid buffer solution, an imidazole buffer solution, a diethanolamine buffer solution, a triethanolamine buffer solution and Good's buffer solutions such as HEPES.

Since the present invention is a reaction rate method of measuring a urea nitrogen amount by using a decrease rate of NADH or NADPH as an index as described above, the measurement is carried out for a short period of time, and it is hardly influenced by interference substances having an ultraviolet absorption in a sample. Moreover, when the sulfhydryl compound is mixed with a sample, the urease inhibition activity thereof is not influenced, and even a high concentration of urea can be accurately quantitatively determined. Further, even in a sample containing polyols such as mannitol, the urease inhibition activity is not eliminated, so that even a sample containing mannitol, from which it has been impossible to obtain an accurate result, can be accurately measured for urea nitrogen, and the method of the present invention is very useful in clinical tests.

The kit of the present invention for measuring urea nitrogen, comprises, as constituents, i) α-ketoglutaric acid (α-KG), ii) reduced-type nicotineamide adenine dinucleotide (NADH) or reduced-type nicotineamide adenine dinucleotide phosphate (NADPH), iii) glutamate dehydrogenase (GLDH)

iv) a sulfhydryl compound, and v) urease.

The origin, concentration, etc., of each constituent are as described in detail concerning the method of the present invention, and they are therefore omitted.

Generally, the kit of the present invention is preferably a combination of a first reagent containing a buffer solution, α-KG, either NADH or NADPH and GLDH, and a second reagent containing a buffer solution, urease and a sulfhydryl compound. That is because, when the first reagent is mixed with a sample first, ammonia present in the sample in advance can be eliminated so that urea nitrogen can be accurately measured. The second reagent may contain α-KG.

EXAMPLES

The present invention will be explained further in detail with reference to Examples and Comparative Example hereinafter.

Example 1

As a first reagent, there was used an aqueous solution containing

| a tris buffer solution | 100 mM |
|---|---|
| α-KG | 12 mM |
| NADPH | 0.3 mM |
| and | |
| GLDH | 10 U/ml | and having a pH of 8.2.

As a second reagent, there was used an aqueous solution containing

| a tris buffer solution | 100 mM |
|---|---|
| α-KG | 12 mM |
| urease | 10 U/ml |
| and | |
| thioglycerol | 400 mM | and having a pH of 8.2.

As samples, there were prepared a sample $M_0$ having an urea nitrogen concentration of 50 mg/dl and a sample $M_5$ containing 20% of mannitol and having an urea nitrogen concentration of 50 mg/dl. Further, the sample $M_5$ was diluted with the sample $M_0$ to prepare samples having mannitol concentrations of 4, 8, 12 and 16% and having an urea nitrogen concentration of 50 mg/dl each, and these samples were used as samples $M_1$, $M_2$, $M_3$ and $M_4$.

The first reagent in an amount of 300 μl was added to 12 μl each of the above samples $M_0$ to $M_5$, and the mixtures were warmed at 37° C. for 5 minutes. Then, 75 μl of the second reagent was added to each of the mixtures, and the mixtures were measured for a change in absorbance at 340 nm per unit time with an automatic analyzer model 7150 supplied by Hitachi Limited. The urea nitrogen concentration in each sample was determined on the basis of a calibration curve prepared in advance. Table 1 and FIG. 1 shows the results.

Comparative Example 1

Urea nitrogen concentrations were determined in the same manner as in Example 1 except that the thioglycerol in the second reagent used in Example 1 was replaced with 75 mM of boric acid. Table 1 and FIG. 1 shows the results.

TABLE 1

| | (Influence by mannitol) | | | | | |
|---|---|---|---|---|---|---|
| Sample, Mannitol concentration | $M_0$ 0% | $M_1$ 4% | $M_2$ 8% | $M_3$ 12% | $M_4$ 16% | $M_5$ 20% |
| Example 1 | 50.4 | 50.7 | 51.0 | 51.3 | 52.1 | 52.4 |
| Comparative Example 1 | 49.9 | 56.0 | 63.5 | 71.8 | 82.1 | 93.3 |

Unit: mg/dl

In FIG. 1, the results in Example 1 are indicated by -○-, those in Comparative Example 1 are indicated by -●-, the axis of ordinates shows urea nitrogen concentrations(mg/dl), and the axis of abscissas shows mannitol concentrations (%)

The results in Table 1 and FIG. 1 show the following. The urease-GLDH method using thioglycerol as an urease inhibitor (Example 1) is free from an influence caused by mannitol in samples and permits accurate measurements of urea nitrogen concentrations as compared with the method using boric acid(Comparative Example 1) as an urease inhibitor.

Example 2

Blood serum containing no polyol was used as samples. The samples were measured by the method of the present invention described in Example 1 and by the method (known method) using boric acid as an urease inhibitor, which is described in the above JP-B-3-65160 and which is considered to have high reliability and generally used in clinical tests, for studying a correlation between the method of the present invention and the above known method. As a result, the method of the present invention was found to have a remarkably significant correlation to the above known method.

According to the present invention, a sample containing mannitol which causes an error in the urea nitrogen measurement based on a reaction rate method can be accurately measured, and further, a sample having a high concentration of urea nitrogen can be measured. The present invention therefore contributes to clinical tests.

What is claimed is:

1. A kit for measuring urea nitrogen, which is a combination of a first reagent comprising:

(i) α-ketoglutaric acid (α-KG),
 (ii) reduced-type nicotineamide adenine dinucleotide (NADH) or reduced-type nicotineamide adenine dinucleotide phosphate (NADPH) and
 (iii) glutamate dehydrogenase (GLDH) and a second reagent comprising:
 (i) urease and
 (ii) a sulfhydryl compound wherein said first reagent and said second reagent includes a buffer solution.

2. The kit of claim 1, wherein the second reagent also contains α-KG.

* * * * *